(12) United States Patent
Ito (10) Patent No.: US 11,994,570 B2
(45) Date of Patent: May 28, 2024

(54) REGION IDENTIFICATION DEVICE, REGION IDENTIFICATION METHOD, AND REGION IDENTIFICATION PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 128 days.

(21) Appl. No.: 17/715,015

(22) Filed: Apr. 6, 2022

(65) Prior Publication Data

US 2022/0229141 A1 Jul. 21, 2022

Related U.S. Application Data

(63) Continuation of application No. PCT/JP2020/033887, filed on Sep. 8, 2020.

(30) Foreign Application Priority Data

Oct. 28, 2019 (JP) .................................. 2019-195705

(51) Int. Cl.
*G01R 33/56* (2006.01)
*G01R 33/563* (2006.01)
*G06T 7/00* (2017.01)

(52) U.S. Cl.
CPC . *G01R 33/56316* (2013.01); *G01R 33/56325* (2013.01); *G06T 7/0012* (2013.01); *G06T 2207/30104* (2013.01)

(58) Field of Classification Search
CPC ........ G01R 33/56316; G01R 33/56325; G01R 33/5608; G06T 7/0012; G06T 2207/30104;

(Continued)

(56) References Cited

U.S. PATENT DOCUMENTS 6,408,201 B1 * 6/2002 Foo .................... A61B 5/704
600/419
2006/0155187 A1 * 7/2006 Zhao ................ G01R 33/56308
600/419

(Continued)

FOREIGN PATENT DOCUMENTS

JP 2016197042 11/2016

OTHER PUBLICATIONS

Martijn Froeling et al., "Machine learning for automatic three-dimensional segmentation of the aorta in 4D flow MRI," ISMRM 27th Annual Meeting & Exhibition, May 2019, pp. 1-3.

(Continued)

*Primary Examiner* — G. M. A Hyder
(74) *Attorney, Agent, or Firm* — JCIPRNET (57) ABSTRACT

An image acquisition unit acquires a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method. An identification unit identifies a region of the structure in the phase contrast image on the basis of a maximum value of the velocity of the fluid between corresponding pixels in each of the phases of the phase contrast image.

9 Claims, 10 Drawing Sheets

(58) Field of Classification Search
CPC ......... G06T 7/0016; G06T 2207/10096; A61B 5/055
See application file for complete search history.

(56) References Cited

U.S. PATENT DOCUMENTS

| | | | |
|---|---|---|---|
| 2006/0235669 A1* | 10/2006 | Charbel | G16H 50/50 703/11 |
| 2016/0239958 A1* | 8/2016 | Bannae | A61B 5/055 |
| 2018/0031662 A1 | 2/2018 | Markl et al. | |
| 2018/0235485 A1* | 8/2018 | Hu | G01R 33/5673 |

OTHER PUBLICATIONS

Michael J Rose et al., "Efficient method for volumetric assessment of peak blood flow velocity using 4D flow MRI," J Magn Reson Imaging., Dec. 2016, pp. 1-21.
"International Search Report (Form PCT/ISA/210) of PCT/JP2020/033887," dated Dec. 1, 2020, with English translation thereof, pp. 1-5.
"Written Opinion of the International Searching Authority (Form PCT/ISA/237)" of PCT/JP2020/033887, dated Dec. 1, 2020, with English translation thereof, pp. 1-6.
Office Action of Japan Counterpart Application, with English translation thereof, dated Jan. 10, 2023, pp. 1-5.

\* cited by examiner

REGION IDENTIFICATION DEVICE, REGION IDENTIFICATION METHOD, AND REGION IDENTIFICATION PROGRAM

CROSS-REFERENCE TO RELATED APPLICATIONS

This application is a Continuation of PCT International Application No. PCT/JP2020/033887 filed on Sep. 8, 2020, which claims priority under 35 U.S.C § 119(a) to Japanese Patent Application No. 2019-195705 filed on Oct. 28, 2019. Each of the above application(s) is hereby expressly incorporated by reference, in its entirety, into the present application.

BACKGROUND OF THE INVENTION

1. Field of the Invention

The present disclosure relates to a region identification device, a region identification method, and a non-transitory computer readable recording medium storing a region identification program that identify a region of a structure inside which fluid flows, such as blood vessels, in an image.

2. Description of the Related Art

In recent years, blood flow in blood vessels has been analyzed by using medical images obtained by imaging the heart, brain, and the like. As a blood flow analysis method using such a medical image, for example, a four-dimensional (4D) flow method that four-dimensionally measures actual blood flow has been used. The 4D flow is a method of deriving a flow velocity vector representing the magnitude and the direction of the velocity of blood flow for each voxel, each pixel, or each region using three-dimensional phase contrast magnetic resonance imaging (MRI) images acquired by imaging a subject including blood vessels over a plurality of time phases (phases) by, for example, a three-dimensional cine phase contrast magnetic resonance method, and of dynamically displaying the flow velocity vector together with the passage of time.

Incidentally, an intensity image (magnitude image) of a part including blood vessels as a target and a phase contrast MRI image (hereinafter, referred to as a phase contrast image) in which a pixel value of each pixel represents the magnitude of the velocity of blood flow in each of x, y, and z directions are acquired by the imaging using the three-dimensional cine phase contrast magnetic resonance method. In order to generate the 4D flow, the flow velocity vector is derived from the magnitude of the velocity of the corresponding pixel positions in the phase contrast images in the three directions of x, y, and z.

In order to generate such a 4D flow, it is necessary to identify a vascular region in the phase contrast image. In order to identify the vascular region, it is necessary to image a subject by magnetic resonance angiography (MRA) or computed tomography angiography (CTA), to acquire an MRA image or a CTA image in which blood vessels are contrast-enhanced, and to perform registration between the MRA image or the CTA image and the phase contrast image. However, the acquisition of the MRA image or the CTA image is time-consuming and costly.

For this reason, it is conceivable to use the intensity image acquired by the imaging using the three-dimensional cine phase contrast magnetic resonance method for identifying blood vessels. However, it is difficult to automatically identify blood vessels in the intensity image because the outline of the structure is very blurred. Therefore, it is necessary to manually identify blood vessels while looking at the intensity image, in a case where the intensity image is used. Meanwhile, it is conceivable to identify blood vessels in the phase contrast image, but the phase contrast image is an image in which the magnitude of the velocity of blood flow in each of the x, y, and z directions is imaged. Therefore, a region where the velocity of blood flow is low appears depending on the phase of the phase contrast image, and as a result, it is difficult to distinguish between blood vessels and the other region in that region.

For this reason, there has been proposed a method of extracting a vascular region from the phase contrast image by means of an extraction model using a neural network (see M. Froeling et al, Machine learning for automatic three-dimensional segmentation of the aorta in 4D flow MRI, ISMRM 2019).

SUMMARY OF THE INVENTION

In the method described in M. Froeling et al, Machine learning for automatic three-dimensional segmentation of the aorta in 4D flow MRI, ISMRM 2019, blood vessels of types used as training data during learning can be accurately extracted from the phase contrast image. However, blood vessels of types other than the blood vessels as learning target cannot be extracted. In addition, it is necessary to prepare a large amount of training data for learning, and it takes time for learning.

The present disclosure has been made in view of the above circumstances, and an object of the present disclosure is to make it possible to easily identify a region of a structure, such as blood vessels, in a phase contrast image.

There is provided a region identification device according to the present disclosure comprising: an image acquisition unit that acquires a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method; and an identification unit that identifies a region of the structure in the phase contrast image on the basis of a maximum value of the velocity of the fluid between corresponding pixels in each of the phases of the phase contrast image.

In the region identification device according to the present disclosure, the identification unit may specify a pixel in which the velocity is highest between corresponding pixels in each of the phases of the phase contrast image, and differences in magnitude and direction of the velocity from surrounding pixels and from a corresponding pixel in at least one adjacent phase are smaller than a reference, and may identify a region consisting of the specified pixels in a high-ranking phase in which the number of the specified pixels correspond to a predetermined number from a top, out of the plurality of phases, as the region of the structure.

Further, in the region identification device according to the present disclosure, the identification unit may specify a maximum phase in which the number of the specified pixels is maximized, and may identify a region consisting of the specified pixels in the maximum phase and at least one phase adjacent to the maximum phase, as the region of the structure.

Further, in the region identification device according to the present disclosure, the identification unit may derive the velocity on the basis of a pixel value in a corresponding pixel of the phase contrast image for each of the three directions.

In addition, the region identification device according to the present disclosure may further comprise a flow velocity vector derivation unit that derives a flow velocity vector representing a magnitude and a direction of the velocity of the fluid in each pixel of the region of the structure, for each of the phases.

In addition, the region identification device according to the present disclosure may further comprise a display control unit that displays a four-dimensional flow of the fluid based on a flow velocity vector for each of the phases on a display unit.

Further, in the region identification device according to the present disclosure, the structure may be a blood vessel and the fluid may be blood.

There is provided a region identification method according to the present disclosure comprising: acquiring a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method; and identifying a region of the structure in the phase contrast image on the basis of a maximum value of the velocity of the fluid between corresponding pixels in each of the phases of the phase contrast image.

The region identification method according to the present disclosure may also be provided as a non-transitory computer readable recording medium storing a program to be executed by a computer.

There is provided another region identification device according to the present disclosure comprising: a memory that stores a command to be executed by a computer; and a processor configured to execute the stored command, in which the processor executes a process including acquiring a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method; and identifying a region of the structure in the phase contrast image on the basis of a maximum value of the velocity of the fluid between corresponding pixels in each of the phases of the phase contrast image.

According to the present disclosure, it is possible to easily identify a region of a structure, such as blood vessels, in a phase contrast image.

DESCRIPTION OF THE PREFERRED EMBODIMENTS

Figure 1:
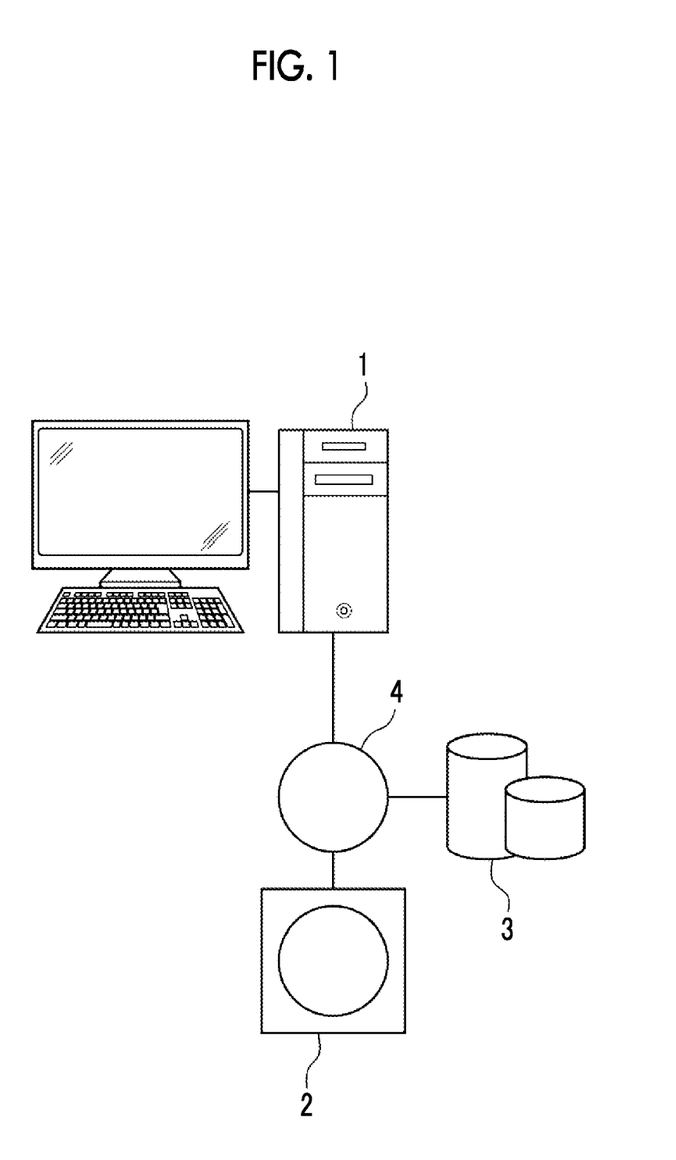
FIG. 1 is a hardware configuration diagram showing the outline of a diagnosis support system to which a region identification device according to an embodiment of the present disclosure is applied.

Hereinafter, an embodiment of the present disclosure will be described with reference to the drawings. FIG. 1 is a hardware configuration diagram showing the outline of a diagnosis support system to which a region identification device according to the embodiment of the present disclosure is applied. As shown in FIG. 1, in the diagnosis support system, a region identification device 1, a three-dimensional image capturing device 2, and an image storage server 3 according to the present embodiment are connected to communicate with each other by way of a network 4.

The three-dimensional image capturing device 2 is a device that images a part of a subject, which is a part to be diagnosed, to generate a three-dimensional image showing the part, and specific examples of the three-dimensional image capturing device 2 are a CT device, an MRI device, and a positron emission tomography (PET) device. The three-dimensional image generated by the three-dimensional image capturing device 2 is transmitted to and stored in the image storage server 3. In the present embodiment, the three-dimensional image capturing device 2 is an MRI device, and the subject is imaged over a plurality of time phases (phases) by a three-dimensional cine phase contrast magnetic resonance method in the MRI device, thereby acquiring three-dimensional images including a three-dimensional phase contrast image and an intensity image that include the aortic arch. The phase contrast image will be described later. Further, the blood vessel that is an aorta corresponds to the structure of the present disclosure, and the blood flow corresponds to the fluid of the present disclosure.

The image storage server 3 is a computer that stores and manages various kinds of data, and comprises a large-capacity external storage device and software for database management. The image storage server 3 communicates with other devices via the wired or wireless network 4 to transmit and receive image data or the like. Specifically, the image storage server 3 acquires various kinds of data including the image data of the three-dimensional image generated by the three-dimensional image capturing device 2 by way of the network, and stores the various kinds of data on a recording medium, such as a large-capacity external storage device, and manages the various kinds of data. A storage format of the image data and the communication between the devices by way of the network 4 are based on a protocol such as digital imaging and communications in medicine (DICOM).

The region identification device 1 is realized by installing a region identification program of the present embodiment on one computer. The computer may be a workstation or a personal computer that is directly operated by a doctor who performs a diagnosis, or may be a server computer connected to the workstation or the personal computer via the network. The region identification program is stored in a storage device of a server computer connected to the network or in a network storage so as to be accessible from the outside, and is downloaded and installed on a computer that the doctor uses in response to a request. Alternatively, the region identification program is distributed by being recorded on a recording medium, such as a digital versatile disc (DVD) or a compact disc read only memory (CD-ROM), and is installed onto the computer from the recording medium.

Figure 2:
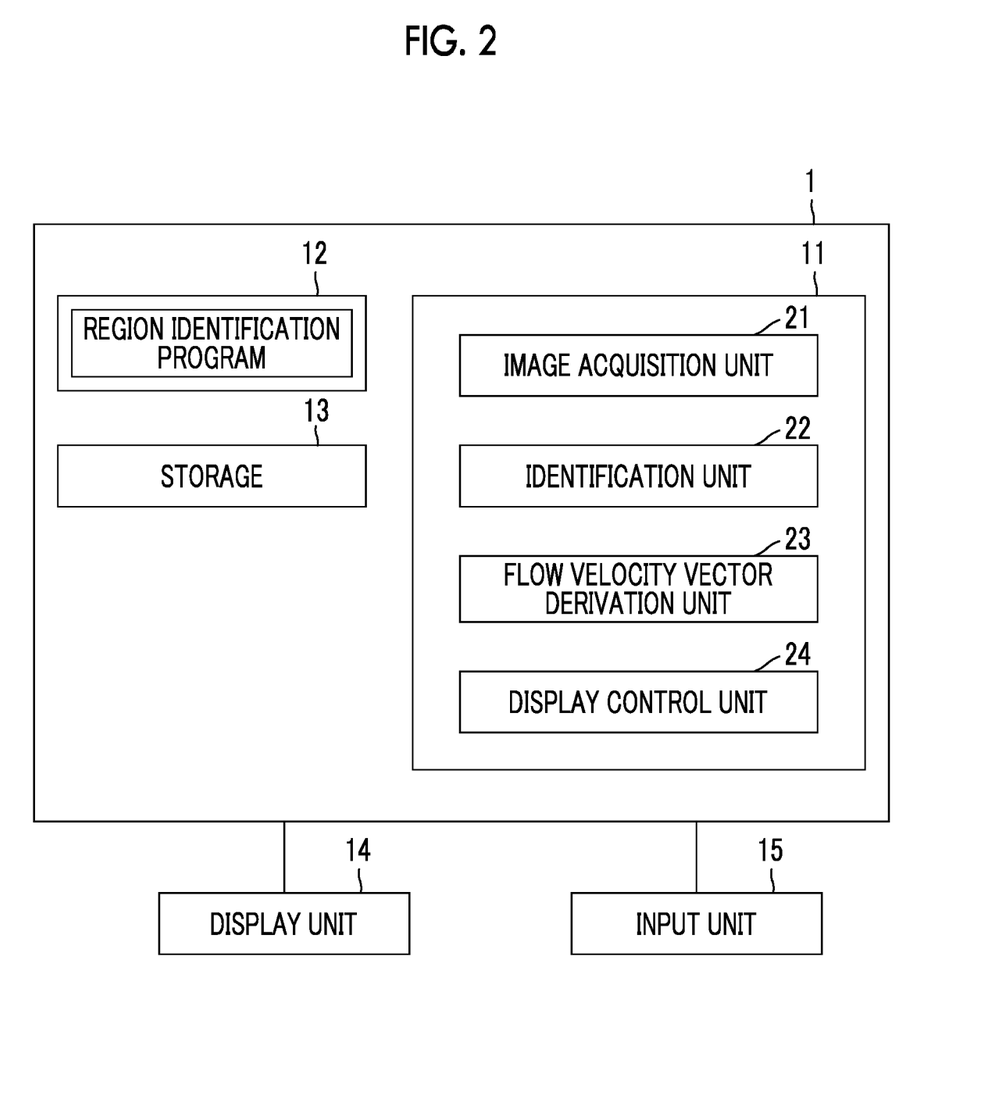
FIG. 2 is a diagram showing the schematic configuration of the region identification device according to the embodiment of the present disclosure.

FIG. 2 is a diagram showing the schematic configuration of the region identification device which is realized by installing the region identification program on a computer. As shown in FIG. 2, the region identification device 1 comprises a central processing unit (CPU) 11, a memory 12, and a storage 13, as a standard workstation configuration. Further, a display unit 14, such as a liquid crystal display, and an input unit 15, such as a keyboard and a mouse, are connected to the region identification device 1.

The storage 13 includes a hard disk drive or the like, and stores three-dimensional images acquired from the image storage server 3 by way of the network 4, and various information including information required for processing.

Further, the region identification program read out from the storage 13 or the like by the CPU or the like is temporarily stored in the memory 12. The region identification program defines, as processing to be executed by the CPU 11, image acquisition processing of acquiring three-dimensional images including a phase contrast image and an intensity image, identification processing of identifying a vascular region in the phase contrast image on the basis of the maximum value of the velocity of blood flow between corresponding pixels in each phase of the phase contrast image, flow velocity vector derivation processing of deriving a flow velocity vector representing the magnitude and the direction of the blood flow in each pixel of the vascular region for each phase of the phase contrast image, and display control processing of displaying a four-dimensional (4D) flow of blood based on the flow velocity vector for each phase on a display unit 14.

Then, the CPU 11 executes the processing in accordance with the program, whereby the computer functions as an image acquisition unit 21, an identification unit 22, a flow velocity vector derivation unit 23, and a display control unit 24.

Figure 3:
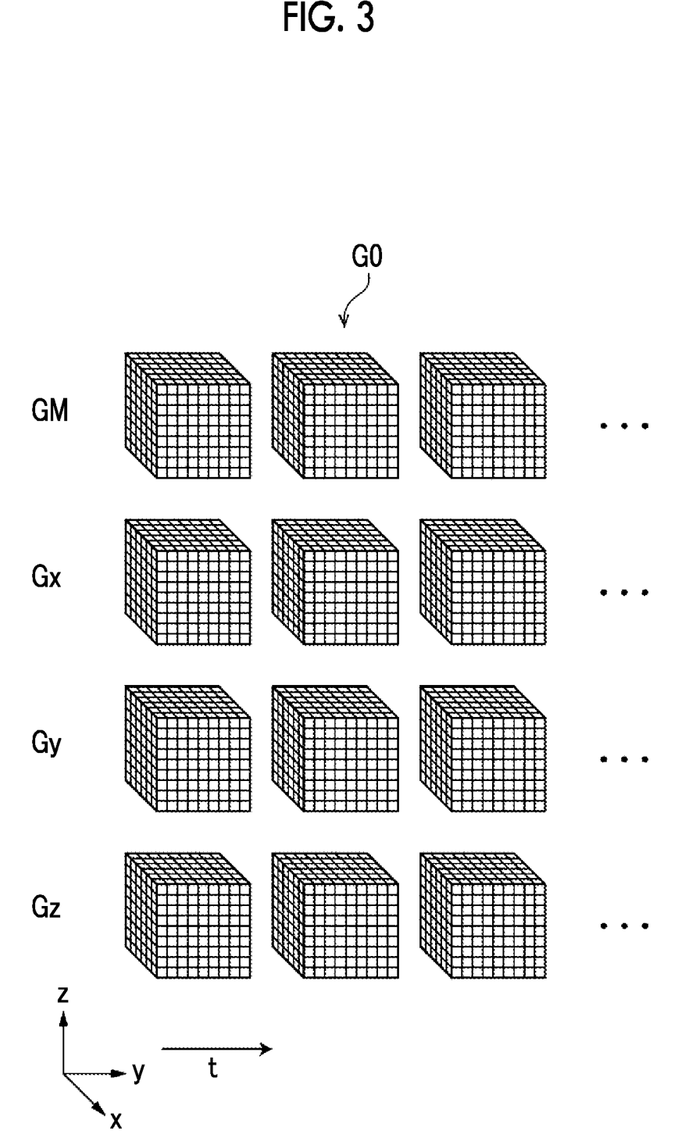
FIG. 3 is a diagram showing a phase contrast image captured by a three-dimensional cine phase contrast magnetic resonance method.

The image acquisition unit 21 acquires three-dimensional images including a phase contrast image and an intensity image from the image storage server 3. In a case where the phase contrast image is already stored in the storage 13, the image acquisition unit 21 may acquire the three-dimensional image from the storage 13. FIG. 3 is a diagram conceptually showing the three-dimensional image. As shown in FIG. 3, a three-dimensional image GO includes an intensity image GM, a phase contrast image Gx in an x-axis direction, a phase contrast image Gy in a y-axis direction, and a phase contrast image Gz in a z-axis direction. The intensity image GM and the phase contrast images Gx, Gy, and Gz are each acquired at a predetermined period along a time axis t. In the present embodiment, a time phase in which each image is acquired on the time axis t is referred to as a phase. Each pixel (voxel) of the intensity image GM has a pixel value corresponding to the composition of the human body. Each pixel (voxel) of the phase contrast images Gx, Gy, and Gz has a pixel value corresponding to the magnitude of the velocity of the blood flow in each axis direction in each phase.

The identification unit 22 identifies a vascular region in the phase contrast images Gx, Gy, and Gz on the basis of the maximum value of the velocity of the blood flow between corresponding pixels in each phase of the phase contrast images Gx, Gy, and Gz. For this purpose, the identification unit 22 first derives a velocity vector in each pixel of the phase contrast images Gx, Gy, and Gz in each phase. The velocity vector represents the magnitude and the direction of the velocity of blood flow in each pixel of the phase contrast images Gx, Gy, and Gz. In a case where the pixel values of the pixels in the phase contrast images Gx, Gy, and Gz are Sx, Sy, and Sz, respectively, the directions of the velocity vectors are directions of (Sx, Sy, Sz) with respect to respective pixels. The magnitude of the velocity vector is derived by $\sqrt{(Sx^2+Sy^2+Sz^2)}$. In the following description, the velocity represents the velocity of blood flow.

Figure 4:
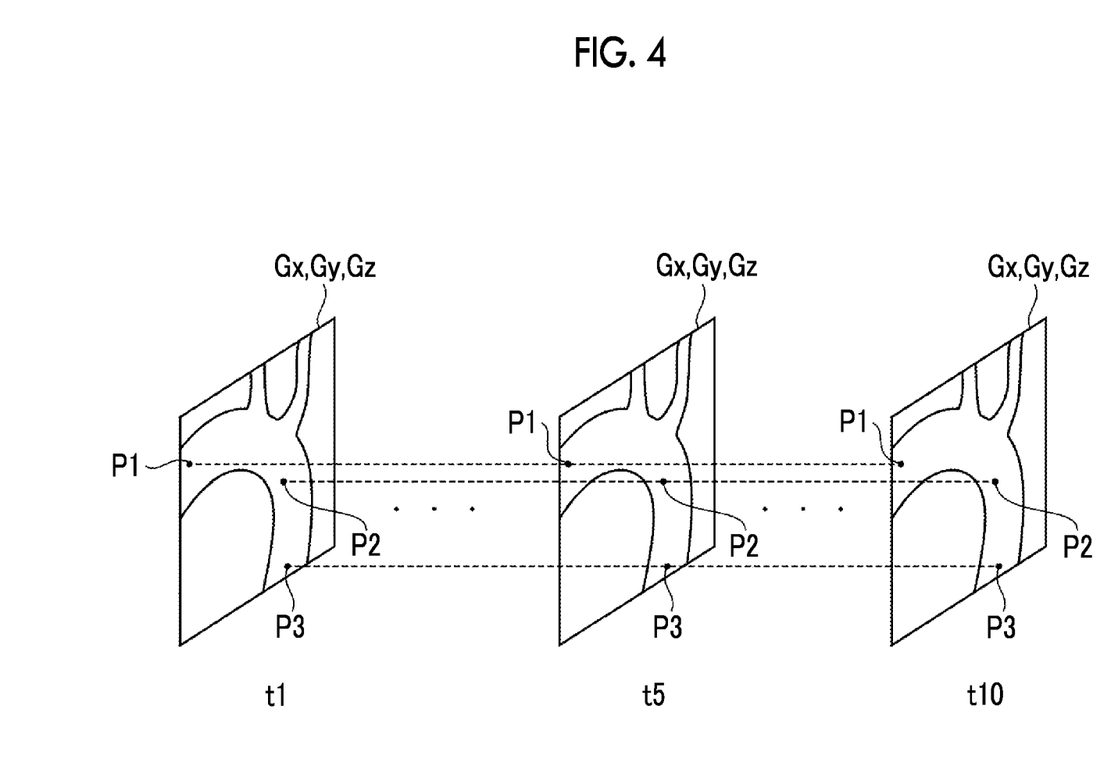
FIG. 4 is a diagram illustrating the specification of a pixel.

Then, the identification unit 22 specifies a pixel in which the velocity is highest between corresponding pixels in each phase of the phase contrast images Gx, Gy, and Gz, and differences in magnitude and direction of the velocity from surrounding pixels and from corresponding pixels of the previous and next phases are smaller than a reference. FIG. 4 is a diagram illustrating the specification of a pixel. In FIG. 4, for the sake of illustration, description will be made assuming that the phase contrast images Gx, Gy, and Gz are assumed to be two-dimensional. Further, in FIG. 4, the phase contrast images Gx, Gy, and Gz consist of 10 phases t1 to t10.

Here, it is assumed that the aortic arch included in the phase contrast images Gx, Gy, and Gz is not moved in all phases. Therefore, pixel positions between the respective phases of the phase contrast images Gx, Gy, and Gz can be associated with each other. Pixels can be associated with each other in all the phases t1 to t10 of the phase contrast images Gx, Gy, and Gz, for example, as in a pixel P1 near the entrance of the aortic arch, a pixel P2 near the middle, and a pixel P3 near the exit, as shown in FIG. 4.

Figure 5:
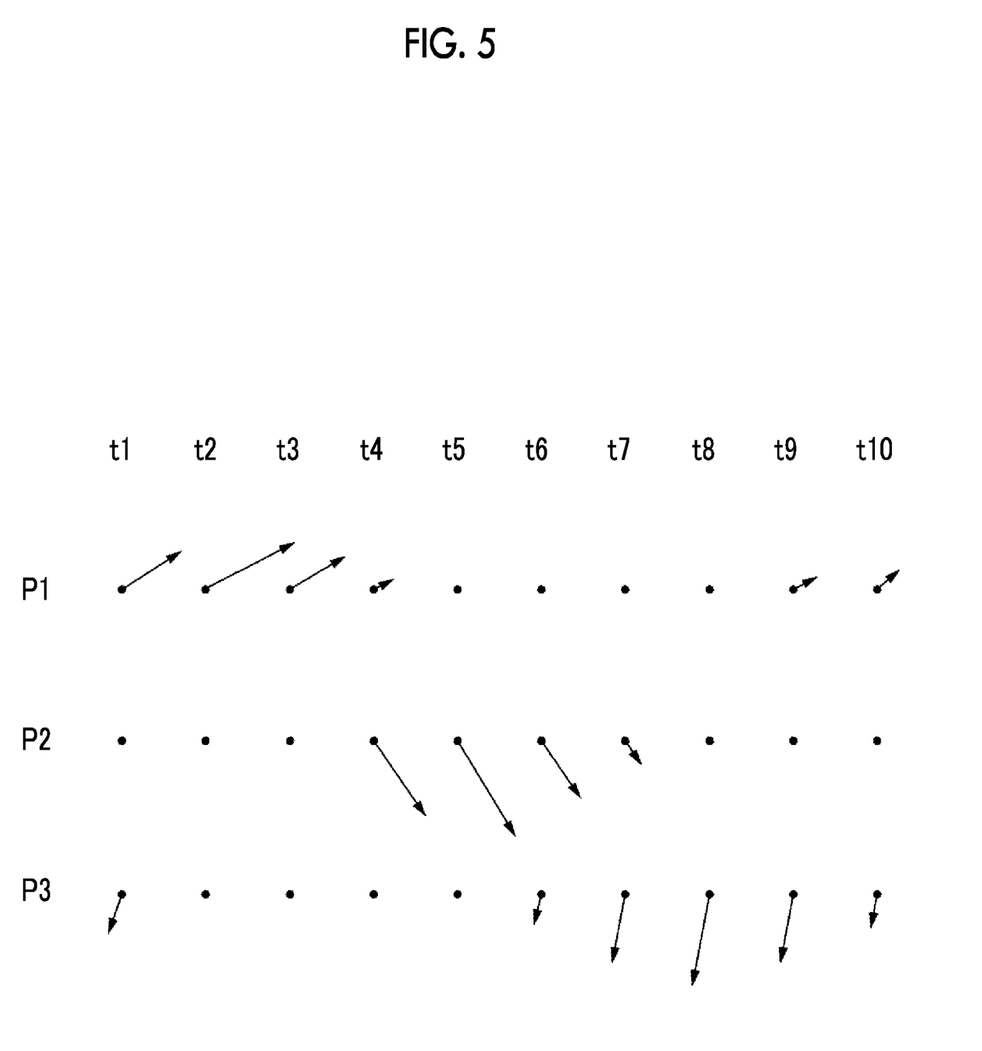
FIG. 5 is a diagram illustrating the specification of a phase in which a velocity is maximized.

The identification unit 22 first specifies a phase in which the velocity is maximized between corresponding pixels in each phase of the phase contrast images Gx, Gy, and Gz. FIG. 5 is a diagram illustrating the specification of the phase in which the velocity is maximized. FIG. 5 shows velocity vectors in each of the phases t1 to t10 of the three pixels P1 to P3 shown in FIG. 4. As shown in FIG. 5, in the pixel P1, the magnitude of the velocity, that is, the magnitude of the velocity vector is maximized in the phase t2. In the pixel P2, the magnitude of the velocity vector is maximized in the phase t5. In the pixel P3, the magnitude of the velocity vector is maximized in the phase t8.

Next, the identification unit 22 specifies, in the phase contrast images Gx, Gy, and Gz of the phase including the pixel having the maximum velocity magnitude (hereinafter, referred to as a maximum pixel), a pixel in which a difference in magnitude and direction of the velocity from pixels around the maximum pixel is smaller than a reference and a difference in magnitude and direction of the velocity from a pixel corresponding to the maximum pixel of at least one phase adjacent to the phase including the maximum pixel is smaller than the reference. Here, the pixels around the maximum pixel are set to pixels in a predetermined range (for example, 5×5×5 pixels) centered on the maximum pixel, but the present disclosure is not limited thereto. Further, the at least one phase adjacent to the phase including the maximum pixel is set to phases immediately before and after the phase including the maximum pixel, but the present disclosure is not limited thereto. The phase adjacent to the phase including the maximum pixel may be only the phase immediately before the phase including the maximum pixel or only the phase immediately after the phase including the maximum pixel. Alternatively, the phase adjacent to the phase including the maximum pixel may be a plurality of phases before and/or after the phase including the maximum pixel.

In the following description, a determination as to whether or not the difference in magnitude and direction of the velocity between the maximum pixel and the pixel around the maximum pixel is smaller than the reference is referred to as a first determination. Further, a determination as to whether or not the difference in magnitude and direction of the velocity from the pixel corresponding to the maximum pixel of at least one phase adjacent to the phase including the maximum pixel is smaller than the reference is referred to as a second determination.

First, the first determination will be described. The identification unit 22 derives the inner product and the ratio of the magnitude of the velocity vector between the velocity vector of the maximum pixel and each of the velocity vectors in the pixels within the predetermined range centered on the maximum pixel. Upon the derivation of the inner product, the unit vector of the velocity vector is used. Then, the identification unit 22 determines whether or not the added value of the inner product and the ratio is a predetermined threshold value Th1 or more. In a case where the determination is affirmative for all the pixels within the predetermined range, the identification unit 22 determines that the difference in magnitude and direction of the velocity between the maximum pixel and the pixels around the maximum pixel is smaller than the reference.

Figure 6:
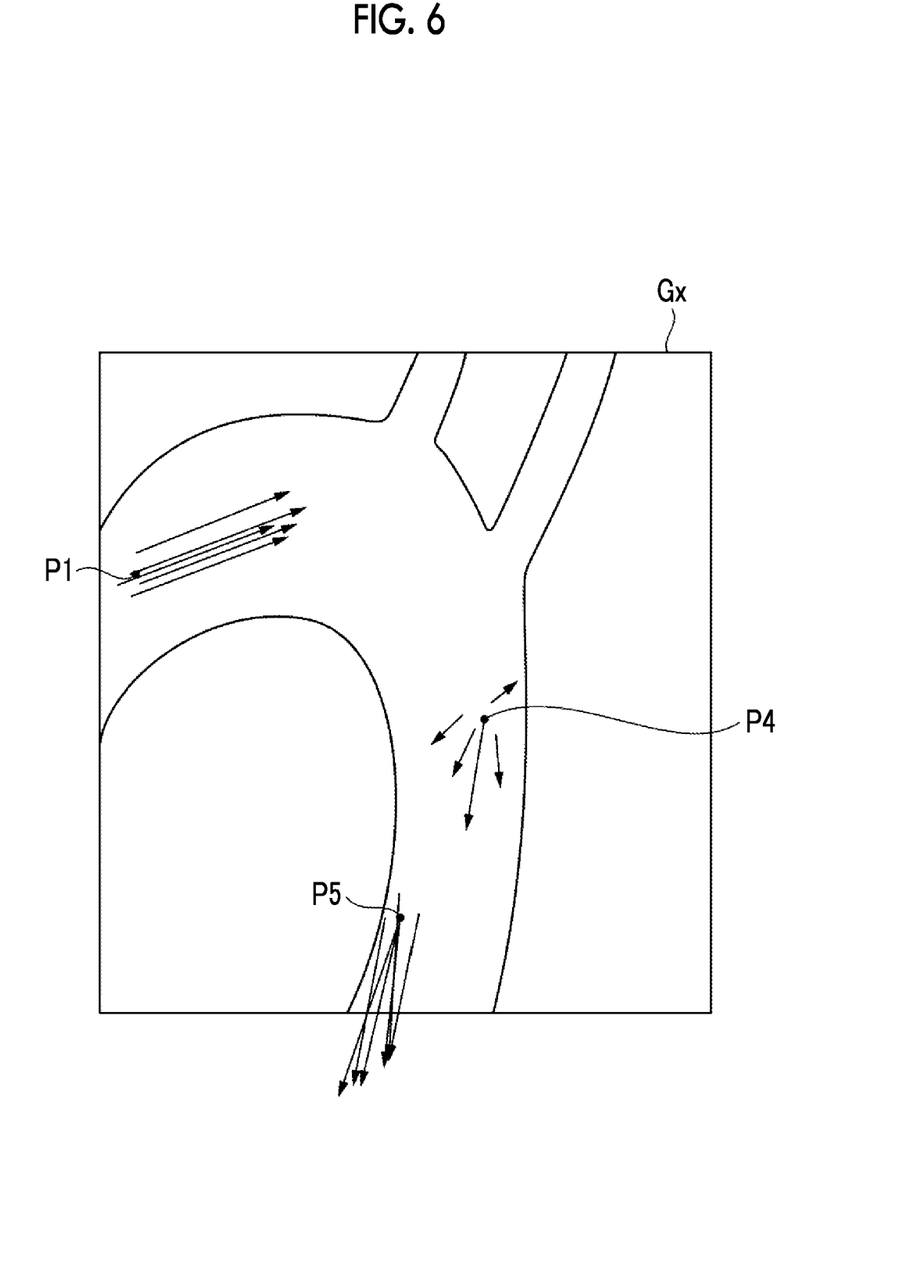
FIG. 6 is a diagram illustrating a first determination.

FIG. 6 is a diagram illustrating the first determination. Although, in FIG. 6, the phase contrast image Gx in a certain phase is used for illustration, in the phase contrast images Gx, Gy, and Gz, only the pixel values are different from each other and the positions of the aortic arch included therein are the same. Therefore, the phase contrast images Gy and Gz may be used. Further, in FIG. 6, for the sake of illustration, only the three pixels P1, P4, and P5 are shown to have the maximum velocities in all phases.

As shown in FIG. 6, in the pixels around the maximum pixels P1 and P5, the velocity vectors (that is, the magnitude and the direction of the velocity) are substantially matched with each other. On the other hand, in the pixels around the maximum pixel P4, the velocity vectors are not matched so much. Therefore, the first determination is affirmative for the maximum pixels P1 and P5, and the first determination is negative for the maximum pixel P4. Accordingly, the identification unit 22 excludes the maximum pixel P4 from the target of the specification of the pixel by the first determination.

Next, the second determination will be described. The identification unit 22 specifies a corresponding pixel corresponding to the maximum pixel in the phase of the maximum pixel (hereinafter, referred to as a target phase) and at least one phase adjacent to the phase of the maximum pixel. Then, the identification unit 22 derives the inner product and the ratio of the magnitude of the velocity vector between the velocity vector of the maximum pixel and the velocity vector of the corresponding pixel. Upon the derivation of the inner product, the unit vector of the velocity vector is used. Then, the identification unit 22 determines whether or not the added value of the inner product and the ratio is a predetermined threshold value Th2 or more. In a case where the determination is affirmative for all the corresponding pixels, the identification unit 22 determines that the difference in magnitude and direction of the velocity between the maximum pixel and the corresponding pixels is smaller than the reference.

Figure 7:
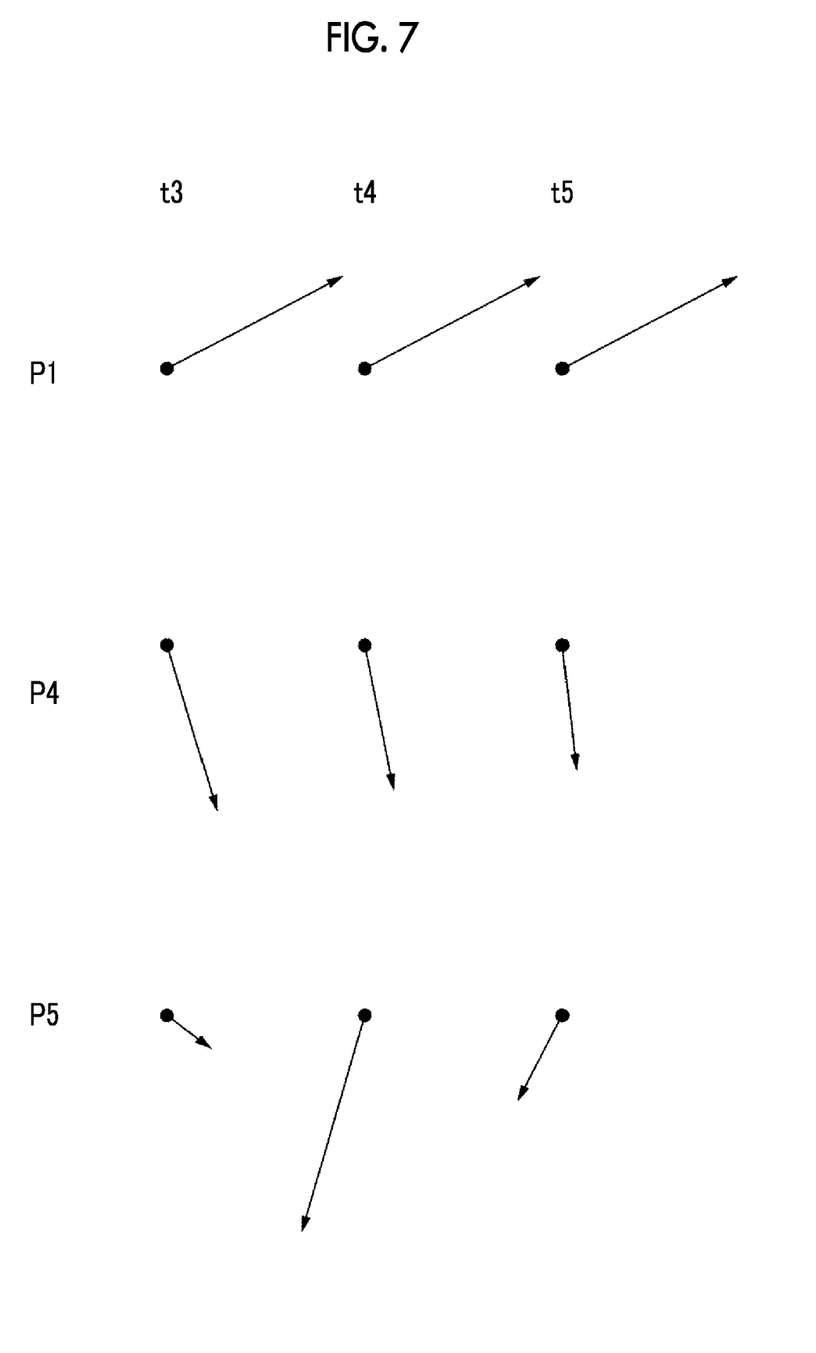
FIG. 7 is a diagram illustrating a second determination.

FIG. 7 is a diagram illustrating the second determination. In FIG. 7, the target phase including the maximum pixel is t4, and the corresponding pixels are included in the phase t3 and the phase t5. As shown in FIG. 7, in the maximum pixels P1 and P4, the velocity vector in the phase t4 is substantially matched with the velocity vectors of the corresponding pixels in the phases t3 and t5. On the other hand, in the maximum pixel P5, the velocity vector in the phase t4 is not matched with the velocity vectors of the corresponding pixels in the phases t3 and t5 so much. Therefore, the second determination is affirmative for the maximum pixels P1 and P4, and the second determination is negative for the maximum pixel P5. Accordingly, the identification unit 22 excludes the maximum pixel P5 from the target of the specification of the pixel by the second determination.

The first and second determinations are made as described above, so that the maximum pixel P1, out of the three maximum pixels P1, P4, and P5 shown in FIGS. 6 and 7, is specified to the pixel in which the differences in magnitude and direction of the velocity from the pixels around the maximum pixel and from the pixel corresponding to the maximum pixel of at least one adjacent phase are smaller than the reference.

The identification unit 22 counts the number of the specified pixels in each phase of the phase contrast images Gx, Gy, and Gz. Then, the identification unit 22 specifies a maximum phase in which the number of the specified pixels is maximized. For example, in a case where the number of the specified pixels in the phase t7 is maximized, out of the 10 phases t1 to t10, the phase t7 is specified to the maximum phase.

Figure 8:
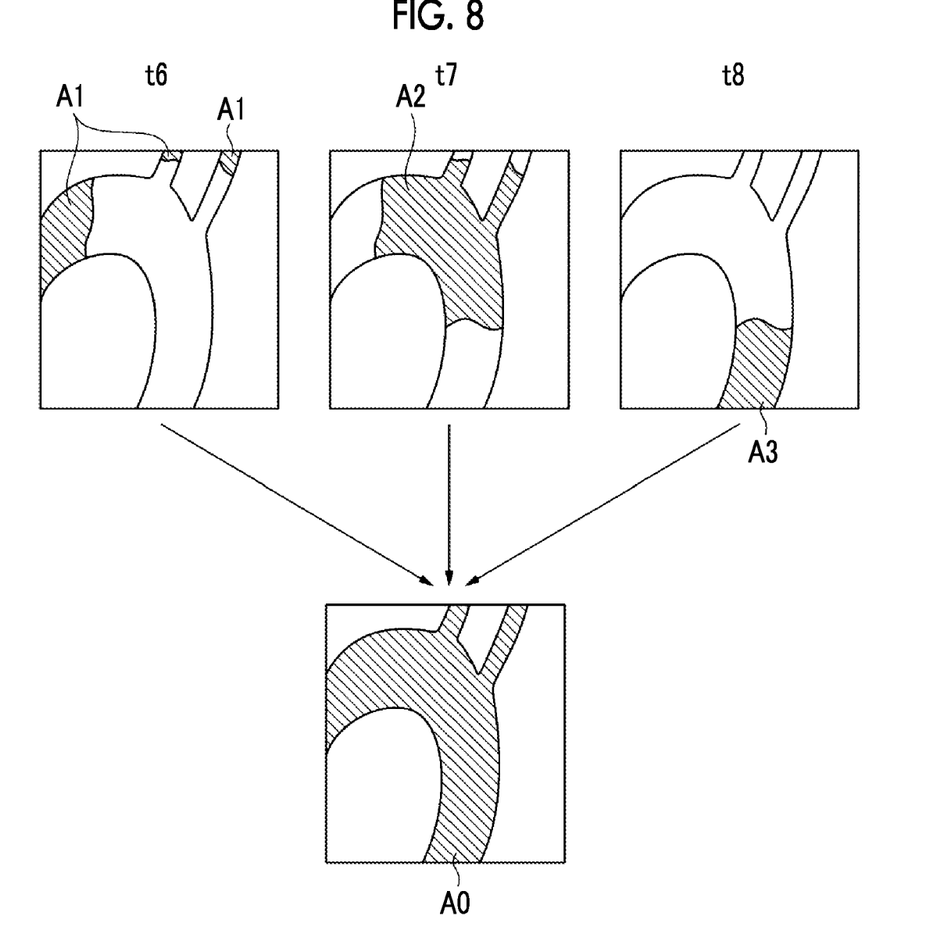
FIG. 8 is a diagram illustrating the identification of a vascular region.

Then, the identification unit 22 identifies a region consisting of the specified pixels in a high-ranking phase in which the number of the specified pixels correspond to a predetermined number from the top, out of the plurality of phases, as the vascular region. In the present embodiment, a region consisting of the specified pixels in the maximum phase specified as described above and at least one phase adjacent to the maximum phase is identified as the vascular region. FIG. 8 is a diagram illustrating the identification of the vascular region. Here, the adjacent phases t6 and t8 before and after the maximum phase t7 are used, but the present disclosure is not limited thereto. Two or more phases before and after the maximum phase may be used, or one or more adjacent phases only before the maximum phase or one or more adjacent phases only after the maximum phase may be used. In the adjacent phases before and after the maximum phase, the number of the specified pixels is smaller than that of the maximum phase, but the number thereof is considerably large. Therefore, one or more adjacent phases before and after the maximum phase are high-ranking phases in which the number of the specified pixels correspond to a predetermined number from the top.

As shown in FIG. 8, a region A1 consisting of the specified pixels is included in the phase t6, a region A2 consisting of the specified pixels is included in the phase t7, and a region A3 consisting of the specified pixels is included in the phase t8. The identification unit 22 identifies a region consisting of the regions A1 to A3 included in the phases t6 to t8, as a vascular region A0.

The flow velocity vector derivation unit 23 derives the flow velocity vector in the vascular region A0. In a case where the pixel values of the corresponding pixels in the vascular regions A0 of the phase contrast images Gx, Gy, and Gz are Vx, Vy, and Vz, respectively, the flow velocity vectors are derived to (Vx, Vy, Vz). The flow velocity vector is the same as the velocity vector, but a vector derived for displaying a 4D flow, which will be described later, is referred to as the flow velocity vector, and a vector derived for identifying the vascular region A0 is referred to as the velocity vector.

Figure 9:
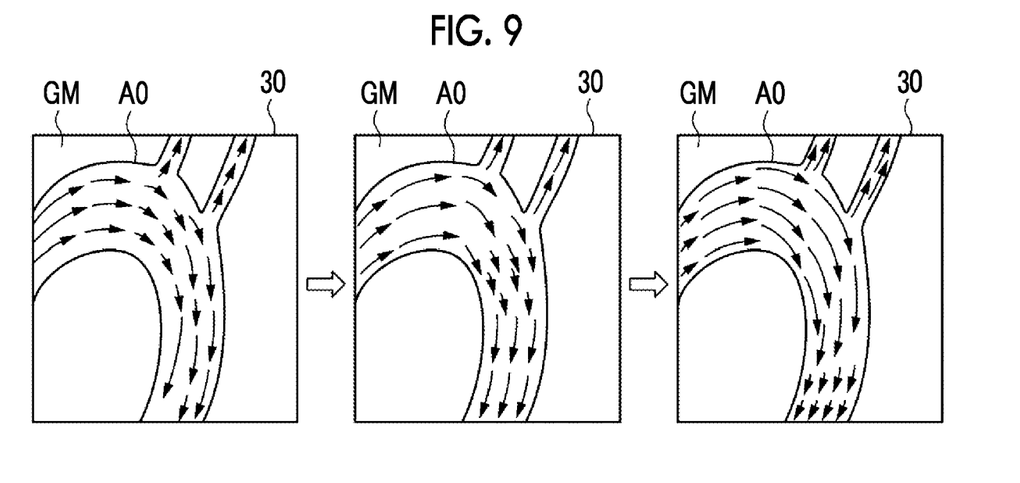
FIG. 9 is a diagram showing a four-dimensional flow.

The display control unit 24 displays the 4D flow of the vascular region A0 on the display unit 14 on the basis of the flow velocity vector derived by the flow velocity vector derivation unit 23. FIG. 9 is a diagram showing the display screen of the 4D flow. As shown in FIG. 9, on a display screen 30 of the 4D flow, the flow velocity vectors are superimposed on the intensity image GM included in the acquired three-dimensional image G0 according to the phase, and are colored in different colors depending on the magnitude of the flow velocity vector. In FIG. 9, the color is omitted, and the state in which the magnitude of the flow velocity vector changes in the three phases is shown. The flow velocity vectors are derived in all the pixels of the vascular region A0. However, upon the display, the flow velocity vectors are appropriately sifted out for display.

Figure 10:
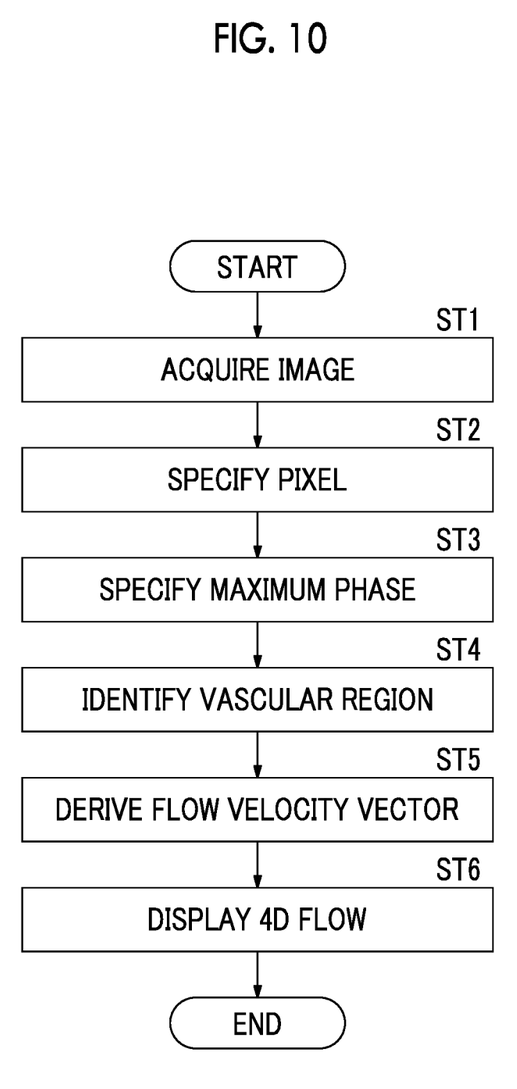
FIG. 10 is a flowchart showing processing performed in the present embodiment.

Next, processing performed in the present embodiment will be described. FIG. 10 is a flowchart showing processing performed in the present embodiment. First, the image acquisition unit 21 acquires three-dimensional images G0 including the phase contrast image and the intensity image from the image storage server 3 (image acquisition; step ST1). In a case where the three-dimensional images G0 are stored in the storage 13, the image acquisition unit 21 acquires the three-dimensional images G0 from the storage 13. Next, the identification unit 22 specifies a pixel in which the velocity is highest between corresponding pixels in each phase of the phase contrast images Gx, Gy, and Gz, and differences in magnitude and direction of the velocity from surrounding pixels and from a corresponding pixel of at least one adjacent phase are smaller than a reference (pixel specification; step ST2).

Further, the identification unit 22 counts the number of the specified pixels in each phase of the phase contrast images Gx, Gy, and Gz, and specifies the maximum phase in which the number of the specified pixels is maximized (step ST3). Then, the identification unit 22 identifies the region consisting of the specified pixels in the maximum phase and at least one phase adjacent to the maximum phase, as the vascular region (step ST4).

Subsequently, the flow velocity vector derivation unit 23 derives the flow velocity vector in the vascular region A0 (step ST5), the display control unit 24 displays the 4D flow of the vascular region A0 on the display unit 14 on the basis of the flow velocity vector derived by the flow velocity vector derivation unit 23 (step ST6), and the processing ends.

As described above, in the present embodiment, the vascular region A0 in the phase contrast image is identified on the basis of the maximum value of the velocity of the blood flow between the corresponding pixels in each phase of the phase contrast image. Therefore, it is possible to identify the vascular region A0 by using only the phase contrast image that is used to generate the 4D flow without acquiring an MRA image or a CTA image. In addition, it is possible to identify the vascular region A0 in the phase contrast image without using the trained extraction model as described in M. Froeling et al, Machine learning for automatic three-dimensional segmentation of the aorta in 4D flow MRI, ISMRM 2019. Consequently, according to the present embodiment, the vascular region in the phase contrast image can be easily identified.

In particular, a pixel in which the velocity is highest between corresponding pixels in each phase of the phase contrast images Gx, Gy, and Gz, and differences in magnitude and direction of the velocity from surrounding pixels and from a corresponding pixel of at least one adjacent phase are smaller than a reference is specified, and the vascular region A0 is identified on the basis of the specified pixel. Therefore, it is possible to identify a region where a velocity vector having a high velocity and a small spatiotemporal variation can be obtained, as the vascular region A0.

Figure 11:
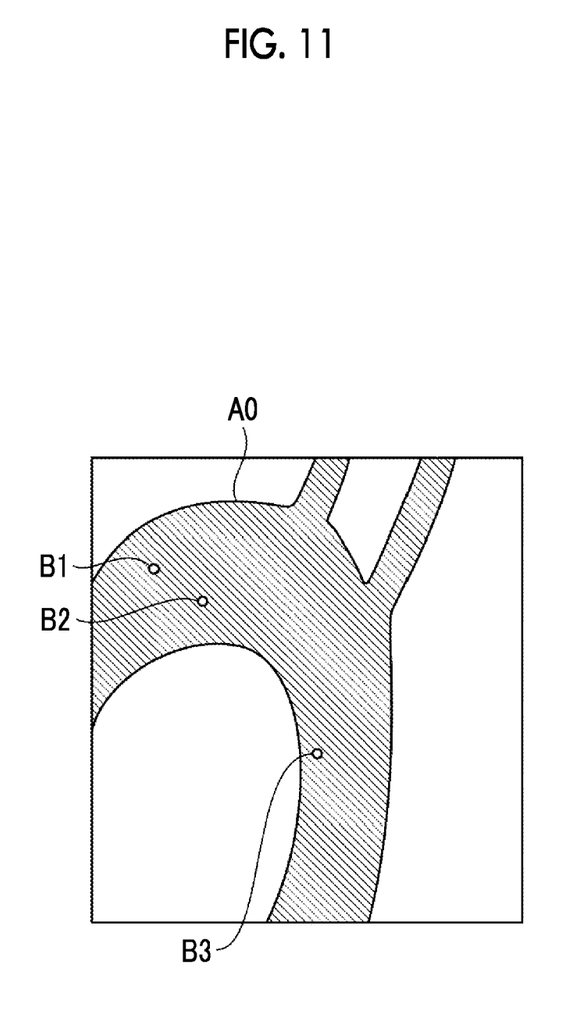
FIG. 11 is a diagram showing a state in which voids exist in the vascular region.

In the above embodiment, in a case where the vascular region A0 is identified, a region consisting of pixels for which at least one of the first determination or the second determination is negative may exist in the vascular region A0. For example, as shown in FIG. 11, void regions B1 to B3 consisting of the pixels for which at least one of the first determination or the second determination is negative may exist in the vascular region A0. In such a case, processing for including the void regions B1 to B3 in the vascular region A0 may be performed. Examples of such processing include dilation processing in morphology operation.

Further, in the above embodiment, the 4D flow of the flow velocity vector is displayed, but the present disclosure is not limited thereto. In addition to the flow velocity vector, 4D flows such as the pressure, vorticity, and helicity of fluid may be displayed.

Further, in the above embodiment, blood vessels are used as the structure inside which fluid flows, but the present disclosure is not limited thereto. For example, in a case where the visualization of the flow of cerebrospinal fluid is considered, as a structure inside which the cerebrospinal fluid flows, the ventricle in the cranium, especially the subarachnoid space, and the spinal cord subarachnoid space in the vertebral canal may be used as the structure inside which the fluid flows. Further, a lymphatic vessel inside which lymph fluid flows may be used.

Further, in the above embodiment, an image targeting a human body is used as a target, but the present disclosure is not limited thereto. For example, it goes without saying that the technique of the present disclosure can be also applied to a case where the flow of a fluid flowing through the inside of a pipe is analyzed.

Further, in the above-described embodiment, for example, as hardware structures of processing units that execute various kinds of processing, such as the image acquisition unit 21, the identification unit 22, the flow velocity vector derivation unit 23, and the display control unit 24, various processors shown below can be used. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU, which is a general-purpose processor that executes software (program) to function as various processing units, as described above.

One processing unit may be formed of one of the various processors or may be formed of a combination of two or more processors of the same type or different types (for example, a combination of a plurality of FPGAs and a combination of a CPU and an FPGA). Alternatively, the plurality of processing units may be formed of one processor.

A first example of the configuration in which the plurality of processing units are formed of one processor is an aspect in which one or more CPUs and software are combined to form one processor and the processor functions as a plurality of processing units. A representative example of the aspect is a computer such as a client and a server. A second example of the configuration is an aspect in which a processor that implements all of the functions of a system including the plurality of processing units with one integrated circuit (IC) chip is used. A representative example of the aspect is a system on chip (SoC). In this manner, various processing units are formed of one or more of the above-described various processors as hardware structures.

More specifically, electrical circuitry obtained by combining circuit elements, such as semiconductor elements, can be used as the hardware structures of these various processors.

EXPLANATION OF REFERENCES

1: region identification device
2: three-dimensional image capturing device
3: image storage server
4: network
11: CPU
12: memory
13: storage
14: display unit
15: input unit
21: image acquisition unit
22: identification unit
23: flow velocity vector derivation unit
24: display control unit
30: display screen
A0: vascular region
A1 to A3: region
B1 to B3: void region
GM: intensity image
Gx, Gy, and Gz: phase contrast image
P1 to P5: pixel

What is claimed is:

1. A region identification device comprising:
a memory that stores a command to be executed by a computer; and
a processor configured to execute the stored command, wherein the processor is configured to:
acquire a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method that excludes magnetic resonance angiography (MRA); and
identify a region of the structure in the phase contrast image on the basis of a maximum value of the velocity of the fluid between corresponding pixels in each of the phases of the phase contrast image.

2. The region identification device according to claim 1, wherein the processor is configured to specify a pixel in which the velocity is highest between corresponding pixels in each of the phases of the phase contrast image, and differences in magnitude and direction of the velocity from surrounding pixels and from a corresponding pixel in at least one adjacent phase are smaller than a reference, and identify a region consisting of the specified pixels in a high-ranking phase in which the number of the specified pixels correspond to a predetermined number from a top, out of the plurality of phases, as the region of the structure.

3. The region identification device according to claim 2, wherein the processor is configured to specify a maximum phase in which the number of the specified pixels is maximized, and identify a region consisting of the specified pixels in the maximum phase and at least one phase adjacent to the maximum phase, as the region of the structure.

4. The region identification device according to claim 1, wherein the processor is configured to derive the velocity on the basis of a pixel value in a corresponding pixel of the phase contrast image for each of the three directions.

5. The region identification device according to claim 1, wherein the processor is configured to derive a flow velocity vector representing a magnitude and a direction of the velocity of the fluid in each pixel of the region of the structure, for each of the phases.

6. The region identification device according to claim 1, wherein the processor is configured to display a four-dimensional flow of the fluid based on a flow velocity vector for each of the phases on a display.

7. The region identification device according to claim 1, wherein the structure is a blood vessel and the fluid is blood.

8. A region identification method comprising:
acquiring a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method that excludes magnetic resonance angiography (MRA); and
identifying a region of the structure in the phase contrast image on the basis of a maximum value of the velocity of the fluid between corresponding pixels in each of the phases of the phase contrast image.

9. A non-transitory computer readable recording medium storing a region identification program causing a computer to execute:
acquiring a phase contrast image consisting of a plurality of phases for each of three spatial directions, in which a pixel value of each pixel represents a velocity of fluid for each of the three directions, the phase contrast image being acquired by imaging a subject including a structure inside which fluid flows by a three-dimensional cine phase contrast magnetic resonance method that excludes magnetic resonance angiography (MRA); and
identifying a region of the structure in the phase contrast image on the basis of a maximum value of the velocity of the fluid between corresponding pixels in each of the phases of the phase contrast image.

* * * * *